(12) United States Patent
Macaulay et al.

(10) Patent No.: US 9,192,751 B2
(45) Date of Patent: Nov. 24, 2015

(54) ELASTIC INTRODUCER SHEATH

(71) Applicant: Medtronic, Inc., Minneapolis, MN (US)

(72) Inventors: Patrick Macaulay, Santa Rosa, CA (US); Stephen Peter, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 225 days.

(21) Appl. No.: 13/791,110

(22) Filed: Mar. 8, 2013

(65) Prior Publication Data

US 2014/0121629 A1     May 1, 2014

Related U.S. Application Data

(60) Provisional application No. 61/719,360, filed on Oct. 26, 2012.

(51) Int. Cl.
*A61M 39/02* (2006.01)
*A61M 25/00* (2006.01)
*A61B 17/34* (2006.01)
*A61M 25/06* (2006.01)

(52) U.S. Cl.
CPC ......... *A61M 39/0247* (2013.01); *A61M 25/005* (2013.01); *A61M 25/0023* (2013.01); *A61B 17/3439* (2013.01); *A61M 25/0662* (2013.01); *A61M 2025/0024* (2013.01); *A61M 2025/0687* (2013.01)

(58) Field of Classification Search
CPC .......... A61M 39/0247; A61M 25/005; A61M 25/0012; A61M 25/0053; A61M 25/0054; A61M 25/0662; A61M 25/0014; A61M 25/0026; A61M 2025/0024; A61M 2025/0025; A61M 2025/0681; A61M 2039/1033; A61B 17/3439; A61B 17/3431; A61F 2/93
See application file for complete search history.

(56) References Cited

U.S. PATENT DOCUMENTS

| 4,601,713 | A | 7/1986 | Fuqua |
| 5,322,519 | A | 6/1994 | Ash |
| 5,458,573 | A | 10/1995 | Summers |
| 5,472,428 | A | 12/1995 | Peters |
| 5,573,508 | A | 11/1996 | Thornton |
| 5,718,693 | A | 2/1998 | Gupta |
| 5,762,604 | A | 6/1998 | Kieturakis |
| 5,772,628 | A | 6/1998 | Bacich et al. |
| 5,797,951 | A | 8/1998 | Mueller |
| 5,810,776 | A | 9/1998 | Bacich et al. |
| 5,911,702 | A | 6/1999 | Romley et al. |
| 5,935,122 | A | 8/1999 | Fourkas et al. |
| 5,997,508 | A | 12/1999 | Lunn et al. |

(Continued)

FOREIGN PATENT DOCUMENTS

| WO | WO 2004/037333 | 5/2004 |
| WO | WO 2010/075565 | 7/2010 |
| WO | WO 2011/035327 | 3/2011 |

OTHER PUBLICATIONS

International Search Report and Written Opinion for International Application No. PCT/US2013/063844, mailed Jan. 3, 2014, 17 pages.

*Primary Examiner* — Jocelin Tanner

(57) ABSTRACT

An elastic percutaneous elastic introducer sheath is disclosed which can locally expand and reduce to accommodate a transcatheter medical device. The elastic introducer sheath includes a non-circumferentially continuous wire structure, a liner, and a jacket.

19 Claims, 12 Drawing Sheets

(56) References Cited

U.S. PATENT DOCUMENTS

| | | | |
|---|---|---|---|
| 6,090,072 A | 7/2000 | Kratoska et al. | |
| 6,183,443 B1 | 2/2001 | Kratoska et al. | |
| 6,197,016 B1 | 3/2001 | Fourkas et al. | |
| 6,312,443 B1 | 11/2001 | Stone | |
| 6,325,812 B1 | 12/2001 | Dubrul et al. | |
| 6,425,908 B2 | 7/2002 | Ravenscroft et al. | |
| 6,428,566 B1 | 8/2002 | Holt | |
| 6,749,600 B1 | 6/2004 | Levy | |
| 6,808,520 B1 | 10/2004 | Fourkas et al. | |
| 6,814,715 B2 | 11/2004 | Bonutti et al. | |
| 7,090,688 B2 | 8/2006 | Nishtala et al. | |
| 7,144,386 B2 | 12/2006 | Korkor et al. | |
| 7,172,620 B2 | 2/2007 | Gilson | |
| 7,192,433 B2 | 3/2007 | Osypka et al. | |
| 7,329,268 B2 | 2/2008 | Van Nguyen et al. | |
| 7,338,518 B2 | 3/2008 | Chobotov | |
| 7,476,232 B2 | 1/2009 | Deal | |
| 7,524,305 B2 | 4/2009 | Moyer | |
| 7,534,250 B2 | 5/2009 | Schaeffer et al. | |
| 7,591,832 B2 | 9/2009 | Eversull et al. | |
| 7,637,893 B2 | 12/2009 | Christensen et al. | |
| 7,699,864 B2 | 4/2010 | Kick et al. | |
| 7,713,193 B2 | 5/2010 | Nance et al. | |
| 7,736,299 B2 | 6/2010 | Klenk et al. | |
| 7,762,995 B2 | 7/2010 | Eversull et al. | |
| 7,766,820 B2 | 8/2010 | Core | |
| 7,780,630 B2 | 8/2010 | Jenson et al. | |
| 7,780,692 B2 | 8/2010 | Nance et al. | |
| 7,879,024 B2 | 2/2011 | Thorstenson et al. | |
| 7,887,733 B2 | 2/2011 | Moyer | |
| 7,892,203 B2 | 2/2011 | Lenker et al. | |
| 7,896,897 B2 | 3/2011 | Gresham et al. | |
| 7,909,798 B2 | 3/2011 | Osypka | |
| 7,927,309 B2 | 4/2011 | Palm | |
| 7,951,110 B2 | 5/2011 | Bishop et al. | |
| 7,963,952 B2 | 6/2011 | Wright, Jr. et al. | |
| 7,967,798 B2 | 6/2011 | Reydel et al. | |
| 7,985,228 B2 | 7/2011 | Phan et al. | |
| 7,985,232 B2 | 7/2011 | Potter et al. | |
| 7,993,350 B2 | 8/2011 | Ventura et al. | |
| 8,034,072 B2 | 10/2011 | Nguyen et al. | |
| 8,092,481 B2 | 1/2012 | Nance et al. | |
| 8,414,645 B2 | 4/2013 | Dwork et al. | |
| 2005/0070881 A1* | 3/2005 | Gribbons et al. | 604/525 |
| 2006/0052750 A1 | 3/2006 | Lenker et al. | |
| 2006/0265056 A1 | 11/2006 | Nguyen et al. | |
| 2007/0021768 A1* | 1/2007 | Nance et al. | 606/192 |
| 2007/0167930 A1 | 7/2007 | Eversull et al. | |
| 2007/0239266 A1 | 10/2007 | Birdsall | |
| 2007/0239269 A1 | 10/2007 | Dolan et al. | |
| 2008/0065011 A1 | 3/2008 | Marchand et al. | |
| 2008/0188928 A1* | 8/2008 | Salahieh et al. | 623/2.11 |
| 2010/0082000 A1 | 4/2010 | Honeck et al. | |
| 2010/0094392 A1* | 4/2010 | Nguyen et al. | 623/1.11 |
| 2011/0251681 A1 | 10/2011 | Shipley et al. | |
| 2012/0083877 A1 | 4/2012 | Nguyen et al. | |

\* cited by examiner

ELASTIC INTRODUCER SHEATH

CROSS-REFERENCE TO RELATED APPLICATION

This application claims benefit under 35 U.S.C. 119(e) to U.S. Provisional Patent Application 61/719,360, filed Oct. 26, 2012, which is incorporated by reference herein in its entirety.

BACKGROUND OF THE INVENTION

1. Field of the Invention

The present invention is related to percutaneous introducer sheaths, in particular a percutaneous elastic introducer sheath designed to introduce a transcatheter device into a patient's vasculature. The percutaneous elastic introducer sheath can accommodate the delivery of transcatheter devices of a range of sizes.

2. Background Art

A percutaneous introducer sheath is used to access the vascular system of a patient and acts as a way to introduce and, position various transcatheter medical devices within the patient. The introducer sheath is a tube-like member which is partially inserted into the vasculature at a puncture site, typically in either the femoral, brachial, or radial artery of the patient. The proximal, or working end, of the introducer sheath is accessible outside of the vasculature for the introduction of transcatheter medical devices through the sheath. A guide wire can be inserted through the introducer sheath and subsequently steered through the vascular system to the site of therapy.

A typical introducer sheath system contains an access lumen for introduction of transcatheter medical devices, a Luer hub for connection to syringes and other peripheral devices, and a hemostasis valve to prevent blood loss from the lumen of the introducer sheath.

Large-profile transcatheter medical devices have traditionally required a larger-profile introducer sheath which provides a fixed internal clearance to allow the device to pass through the patient's vasculature. Such procedures using the large-profile transcatheter medical devices, typically through the femoral artery, are therefore limited to patients with sufficient vessel size to accommodate the introducer sheath. In order to extend the availability of large-profile transcatheter devices to patients with smaller vessel sizes, an introducer with a smaller profile that locally expands within the patient's vasculature to allow passage of the large-profile transcatheter device is desired. Local expansion and subsequent recoil of the elastic introducer profile is less traumatic on the patient's vessel than a sustained expansion for a large-profile introducer sheath.

BRIEF SUMMARY OF THE INVENTION

Provided herein is an elastic percutaneous introducer sheath that generally includes a liner, a wire structure, and a jacket having a longitudinal gap. The elastic introducer can be locally expanded once in situ and can elastically recoil to a reduced diameter. The wire structure within the introducer allows expansion of the introducer, especially when passing the largest part of the transcatheter medical device being introduced. By use of the wire structure, only the part of the introducer with the largest portion of the device is expanded. Once the transcatheter device is passed, the wire structure acts as a spring to fully or partially collapse the diameter of the introducer.

In view thereof, disclosed herein are aspects of an elastic introducer sheath including a non-circumferentially continuous wire structure extending along a length of the access device, a first biocompatible material layer connected to the wire structure, the wire structure and the first layer having a longitudinal gap in an expanded configuration, and a circumferentially continuous second biocompatible material layer connected to the first layer.

In another exemplary embodiment, disclosed herein are aspects of a method for percutaneously introducing a medical device into a patient's body including percutaneously introducing a distal end of an elastic surgical access device into the patient's body, the elastic surgical access device including a non-circumferentially continuous wire structure extending along a length of the access device, a first biocompatible material layer, and a second biocompatible material layer; passing the medical device through the access device; expanding a section of the access device from a first diameter to a second larger diameter approximately equal to the outer diameter of the medical device as the medical device passes through the section of the access device; and contracting the access device from the second diameter after the medical device passes through the section of the access device.

BRIEF DESCRIPTION OF THE DRAWINGS/FIGURES

The accompanying figures, which are incorporated herein, form part of the specification and illustrate embodiments of an elastic surgical access device. Together with the description, the figures further serve to explain the principles of and to enable a person skilled in the relevant art(s) to make and use the elastic surgical access device described herein. In the drawings, like reference numbers indicate identical or functionally similar elements.

DETAILED DESCRIPTION OF THE INVENTION

Figure 1:
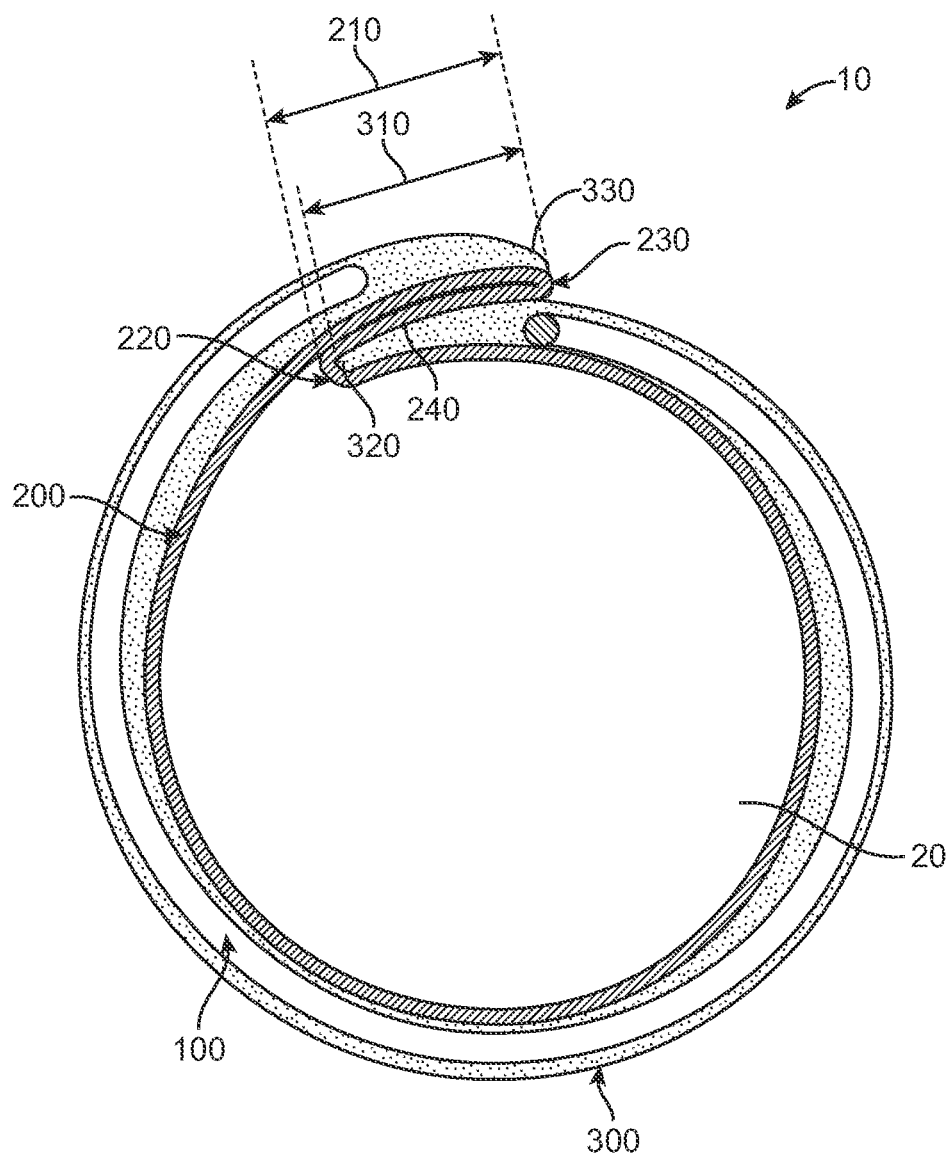
FIG. 1 is a sectional view of an elastic introducer according to an aspect of this disclosure.

The following detailed description of an elastic surgical access device refers to the accompanying figures that illustrate exemplary embodiments. Other embodiments are possible. Modifications can be made to the embodiments described herein without departing from the spirit and scope of the present invention. Therefore, the following detailed description is not meant to be limiting.

Referring to FIGS. 1 and 14-17, introducer system 1 includes an elastic introducer 10 that has a proximal end 12 and a distal end 14. Elastic introducer 10 includes a wire structure 100, a liner 200, and a jacket 300. In one aspect of the invention, wire structure 100 is laminated between liner 200 and jacket 300. In an alternate aspect, wire structure 100 is embedded within jacket 300. Wire structure 100 provides kink resistance for elastic introducer 10 and also allows elastic introducer 10 to actively recoil to a reduced diameter after passage of a transcatheter medical device through a portion of elastic introducer 10. Elastic introducer 10 includes a full diameter section 70 adjacent to hub 15 at proximal end 12. In full diameter section 70, wire structure 100 is coiled. In full diameter section 70, jacket 200 and liner 300 are circumferentially continuous and concentric with coiled wire structure 101. Elastic introducer 10 also includes an expandable transition section 80 and an expandable section 90. Expandable transition section 80 tapers the diameter of elastic introducer 10 from full diameter section 70 to expandable section 90. In expandable transition section 80 and expandable section 90, wire structure 100 is bent around a longitudinal axis into a C-shaped wire structure 103 forming a series of non-continuous circumferential loops. In one aspect of the invention, jacket 300 and C-shaped wire structure 103 are not circumferentially continuous in expandable transition section 80 and expandable section 90 and include a longitudinal gap visible in an expanded configuration. Expandable transition section 80 facilitates a smooth transition from hub 15 and full diameter section 70 to expandable section 90.

Typically, elastic introducer 10 is inserted into a vessel, such as the femoral artery, passing through the skin of a patient, such that the distal end 14 of elastic introducer 10 is inserted into the vessel. In one aspect of the invention. elastic introducer 10 includes a tapered tip for insertion through the vessel wall without roll back of the tip. Elastic introducer 10 can also include a suture eyelet for suture attachment to tissue. In a further aspect of the invention, elastic introducer 10 can be used with a guide wire. In one aspect, elastic introducer 10 can be compatible with a 0.035 inch guide wire.

Figure 9:
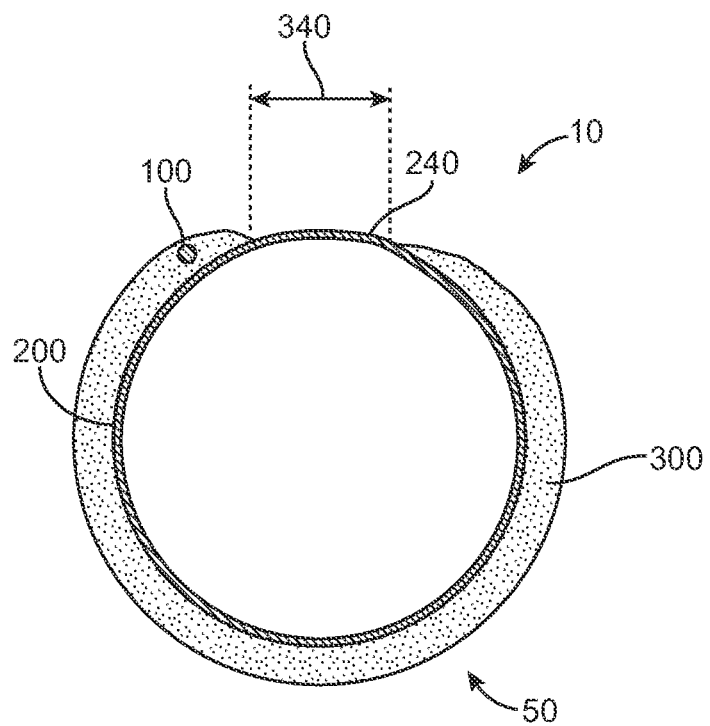
FIG. 9 is a sectional view of an elastic introducer according to an aspect of this disclosure.
Figure 10:
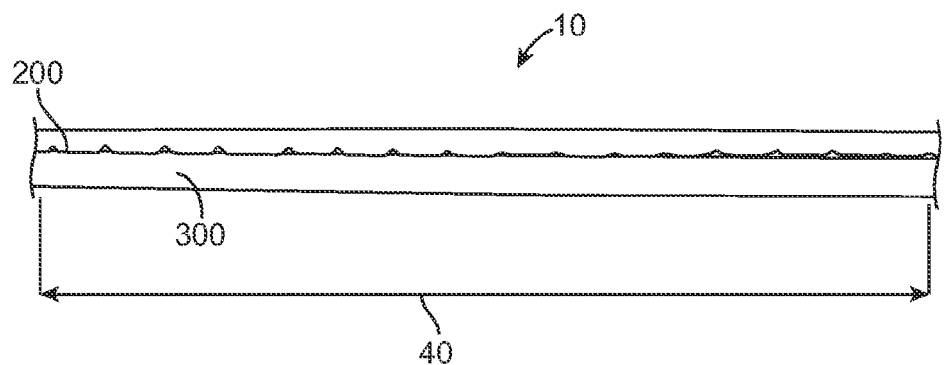
FIG. 10 is a top view of an elastic introducer according to an aspect of this disclosure.
Figure 11:
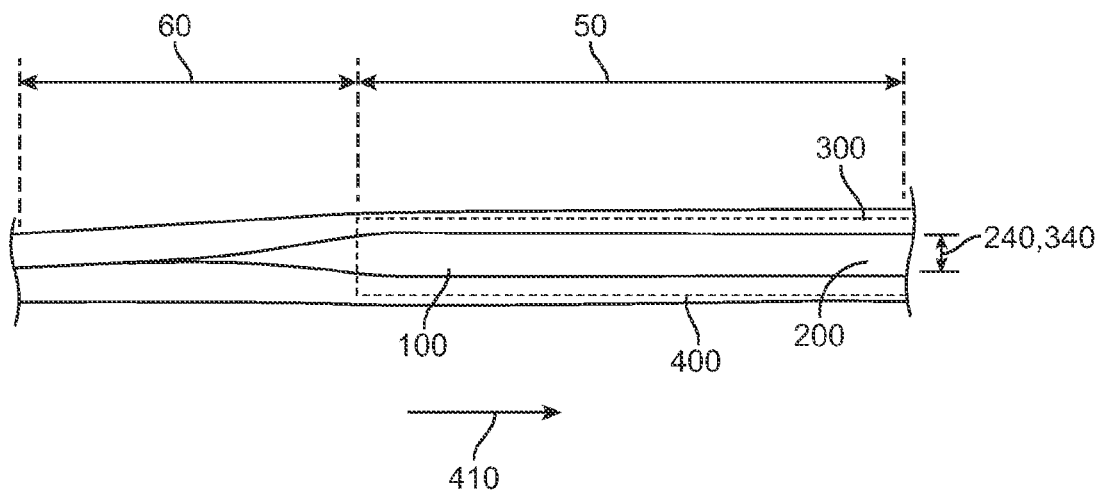
FIG. 11 is a top view of an elastic introducer according to an aspect of this disclosure.
Figure 12:
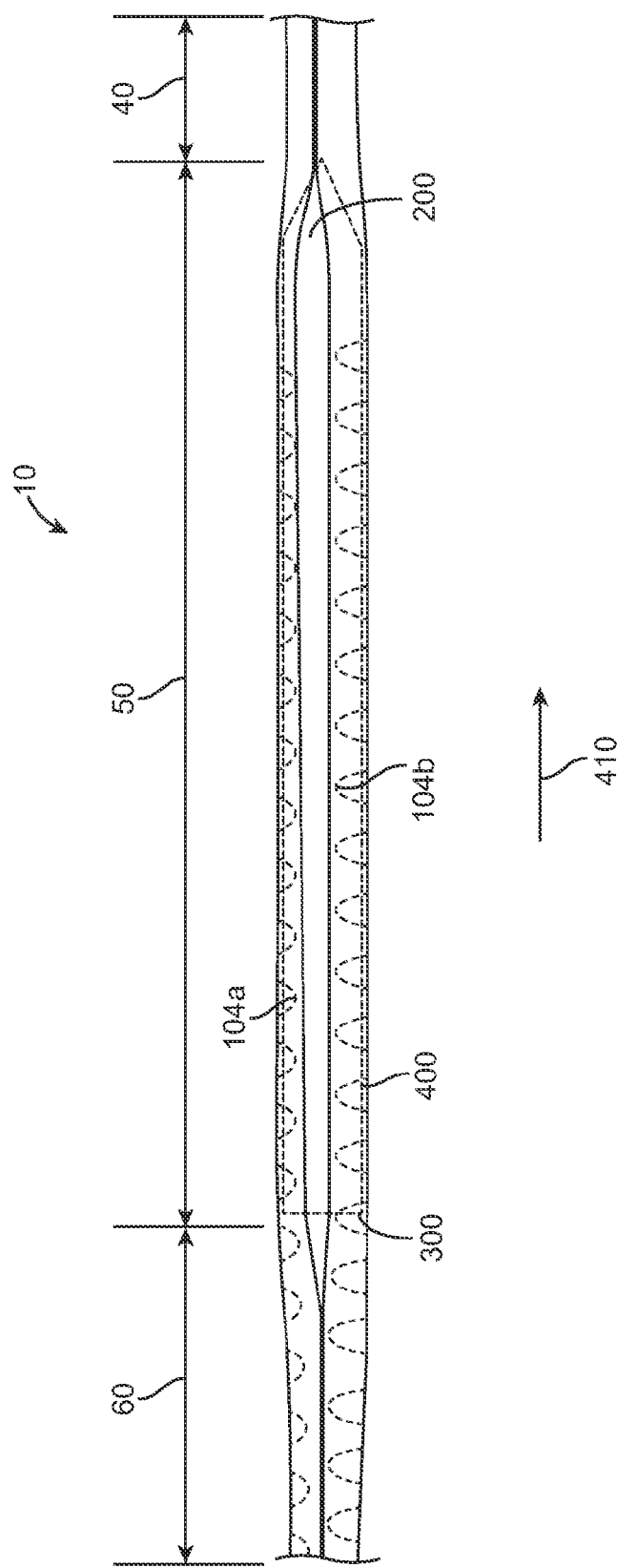
FIG. 12 is a top view of an elastic introducer according to an aspect of this disclosure.
Figure 13:
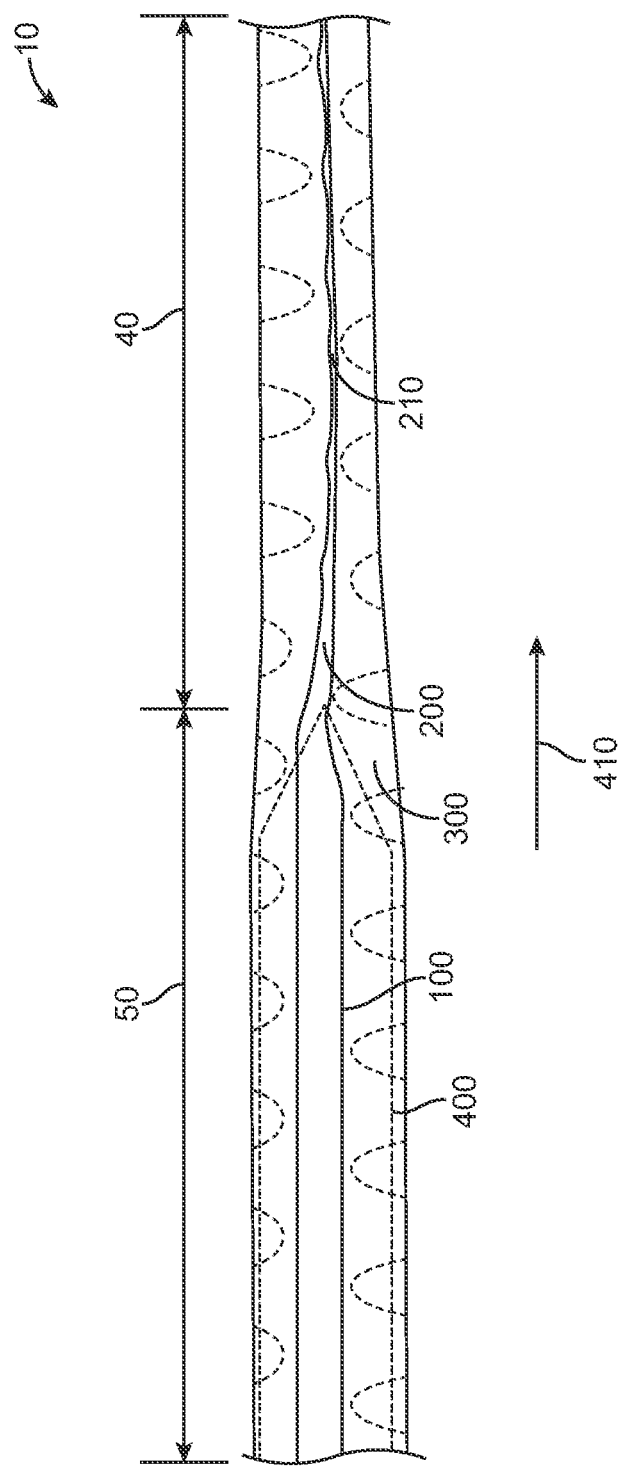
FIG. 13 is a top view of an elastic introducer according to an aspect of this disclosure.
Figure 14:
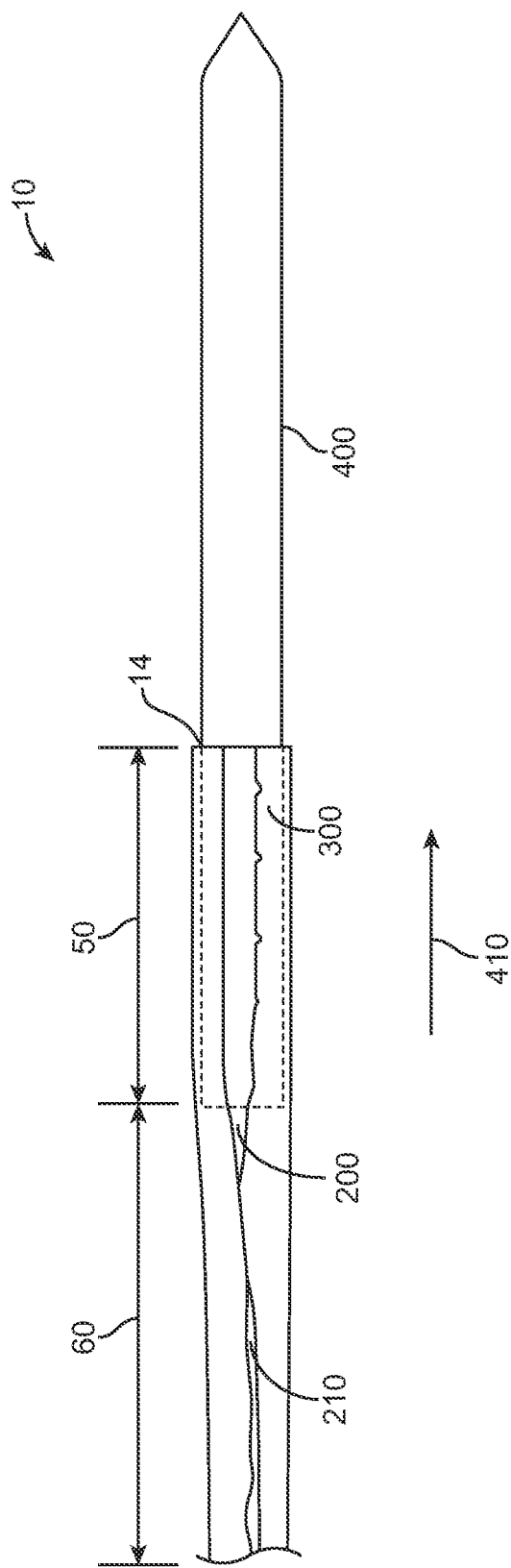
FIG. 14 is a top view of an elastic introducer according to an aspect of this disclosure.
Figure 16:
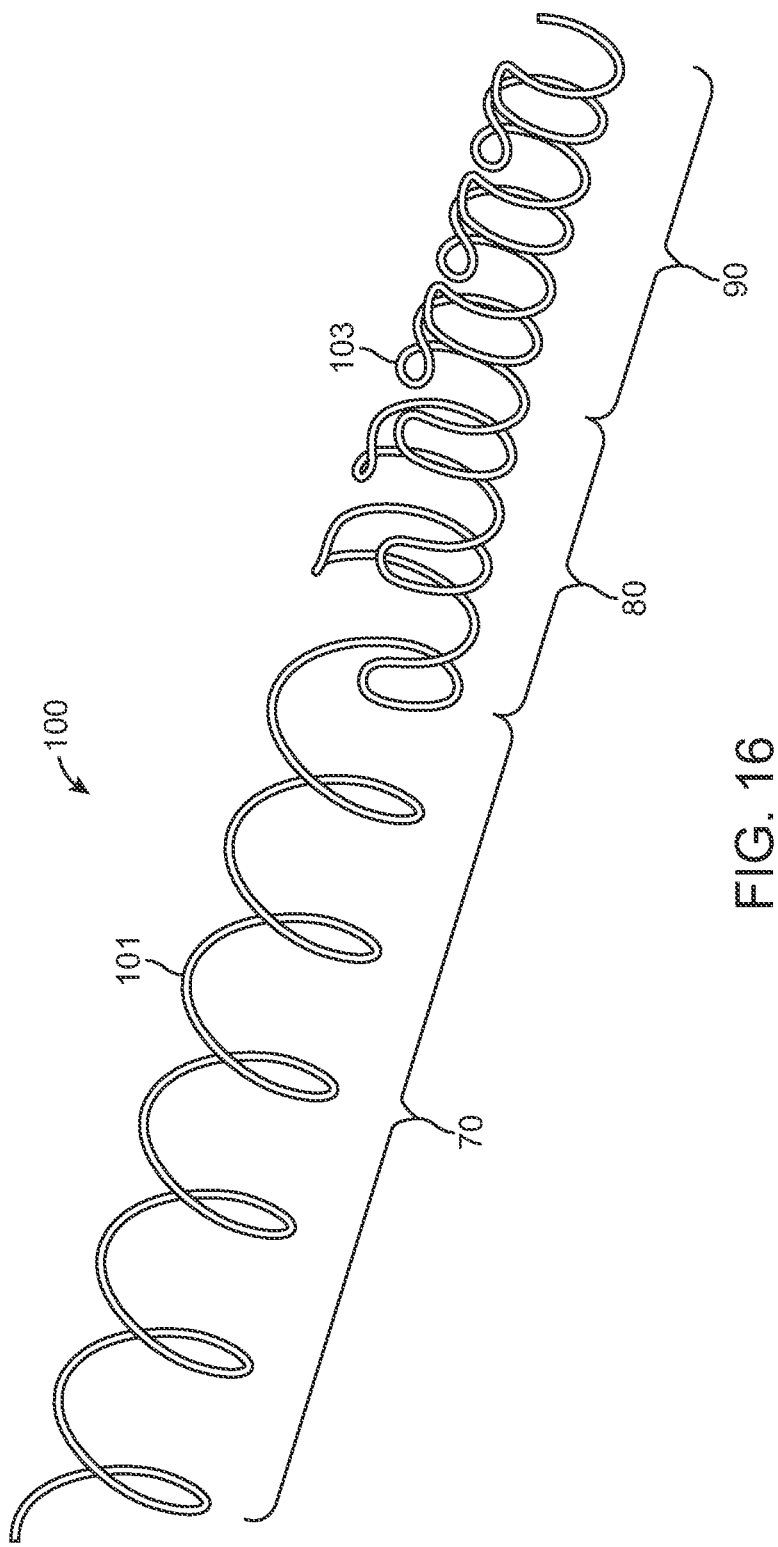
FIG. 16 is a perspective view of a wire structure of an elastic introducer according to an aspect of the disclosure.
Figure 17:
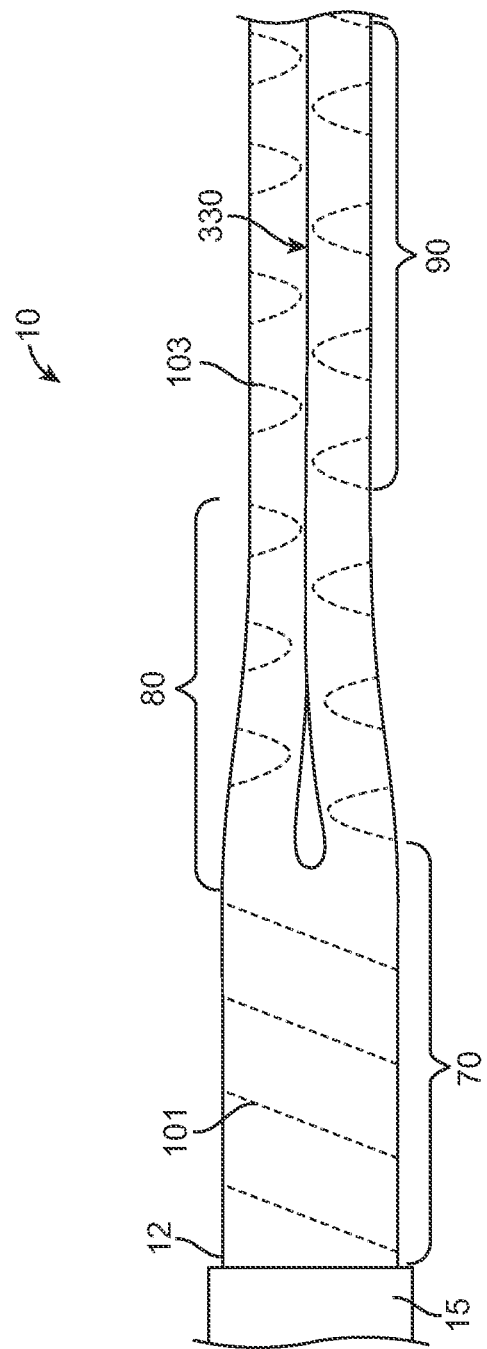
FIG. 17 is a top view of an elastic introducer according to an aspect of this disclosure.

In one aspect of the invention, liner 200 is circumferentially continuous and forms a lumen 20. In this aspect, wire structure 100 and jacket 300 are not circumferentially continuous and include a longitudinal gap visible in an expanded configuration. As shown in FIGS. 1 and 16-17, in a collapsed configuration, elastic introducer 10 includes a liner overlap region 210 and a jacket overlap region 310 in expandable transition section 80 and expandable section 90. Liner overlap region 210 includes liner gap portion 240 defined by an inner fold 220 and an outer fold 230 of liner 200. Liner gap portion 240 can be at least partially covered by jacket 300. In one aspect of the invention, liner 200 extends around inner edge 320 to form inner fold 220. Jacket overlap region 310 is defined by inner edge 320 and outer edge 330 of jacket 300. In an expanded configuration, inner edge 320 and outer edge 330 are separated longitudinally to form a jacket gap 340 (FIG. 9). In such a configuration, inner fold 220 and outer fold 230 are flattened to allow liner gap portion 240 to extend across jacket gap 340.

In one aspect of the invention, liner 200 is tetrafluoroethylene (TFE). In alternate aspects of the invention, liner 200 can be Teflon®, polytetrafluoroethylene (PTFE), polyethylene, polyethylene terephthalate (PET), or polyester. Liner 200 can have a low coefficient of friction on its inner surface to facilitate advancement of a transcatheter medical device through the elastic introducer 10.

In one aspect of the invention, jacket 300 is polyurethane (e.g. Pellethane®, Elasthane™, Texin®, or Tecothane®) and can include 20% barium sulfate added as a radipacifier. In alternate aspects, jacket 300 can be a polyamide polyether block copolymer such as Pebax®, nylon 12, or polyethylene. The material for jacket 300 can also be loaded with tungsten or bismuth subcarbonate to add radiopacity so that elastic introducer 10 can be radio detectable (radiopaque).

Wire structure 100 can be nickel titanium, Nitinol, with the diameter of the wire ranging from approximately 0.005 inches to approximately 0.02 inches. In alternate aspects of the invention, wire structure 100 can be nickel-cobalt-chromium-molybdenum (MP35N), stainless steel, high spring temper steel, or any other metal or composite having elastic properties to permit extension and recoil of elastic introducer 10.

Figure 2:
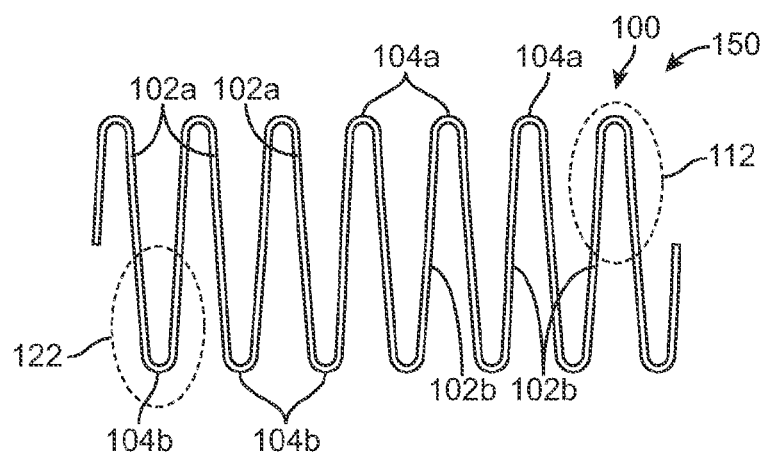
FIG. 2 is a front view of a wire structure of an elastic introducer according to an aspect of this disclosure.
Figure 3:
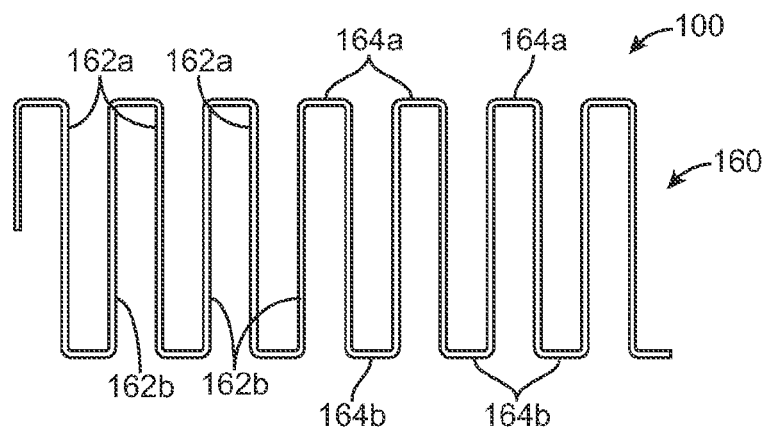
FIG. 3 is a front view of a wire structure of an elastic introducer according to an aspect of this disclosure.
Figure 4:
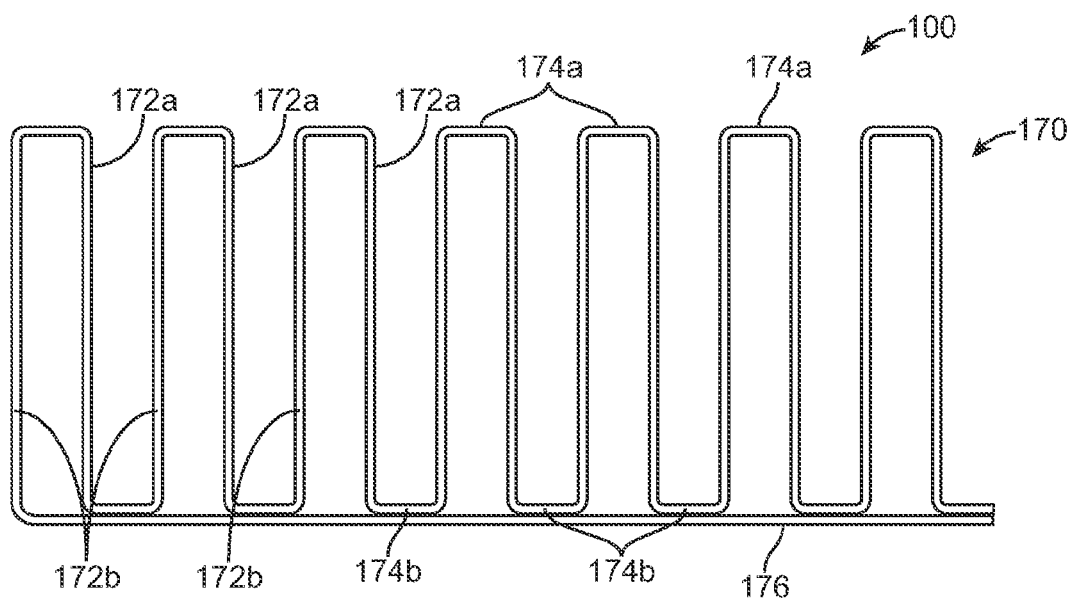
FIG. 4 is a front view of a wire structure of an elastic introducer according to an aspect of this disclosure.

Referring now to FIGS. 2-4, wire structure 100 includes a repeating longitudinal pattern and is shown in a flat or uncurved state. For example, wire structure 100 can include a sinusoid pattern 150 (FIG. 2), a square pattern 160 (FIG. 3), or a modified square pattern 170 including a spine 176 (FIG. 4). Sinusoid pattern 150 includes a series of alternating adjacent straight portions 102a and 102b. Each straight portion 102a is joined to a first adjacent straight portion 102b by a first bent end portion 104a and to a second adjacent straight portion 102b by a second bent end portion 104b. Conversely, each straight portion 102b is joined to two straight portions 102a by first bent end portion 104a and second bent end portion 104b.

Square pattern 160 includes a series of alternating adjacent straight portions 162a and 162b. Each straight portion 162a is joined to a first adjacent straight portion 162b by a first end portion 164a and to a second adjacent straight portion 162b by a second end portion 164b. Conversely, each straight portion 162b is joined to two straight portions 162a by first end portion 164a and second end portion 164b.

Modified square pattern 170 includes a series of alternating adjacent straight portions 172a and 172b. Each straight portion 172a is joined to a first adjacent straight portion 172b by a first end portion 174a and to a second adjacent straight portion 172b by a second end portion 174b. Conversely, each straight portion 172b is joined to two straight portions 172a by first end portion 174a and second end portion 174b. Spine 176 extends along end portions 174b. Spine 176 adds additional tensile rigidity to wire structure 100. In a further aspect of the invention, end portions 174b adjacent spine 176 can be welded or otherwise fixed to spine 176.

The below discussion refers to sinusoidal portion 150 of wire structure 100, however square pattern 160 or modified square pattern 170 could also be used for wire structure 100.

Figure 5:
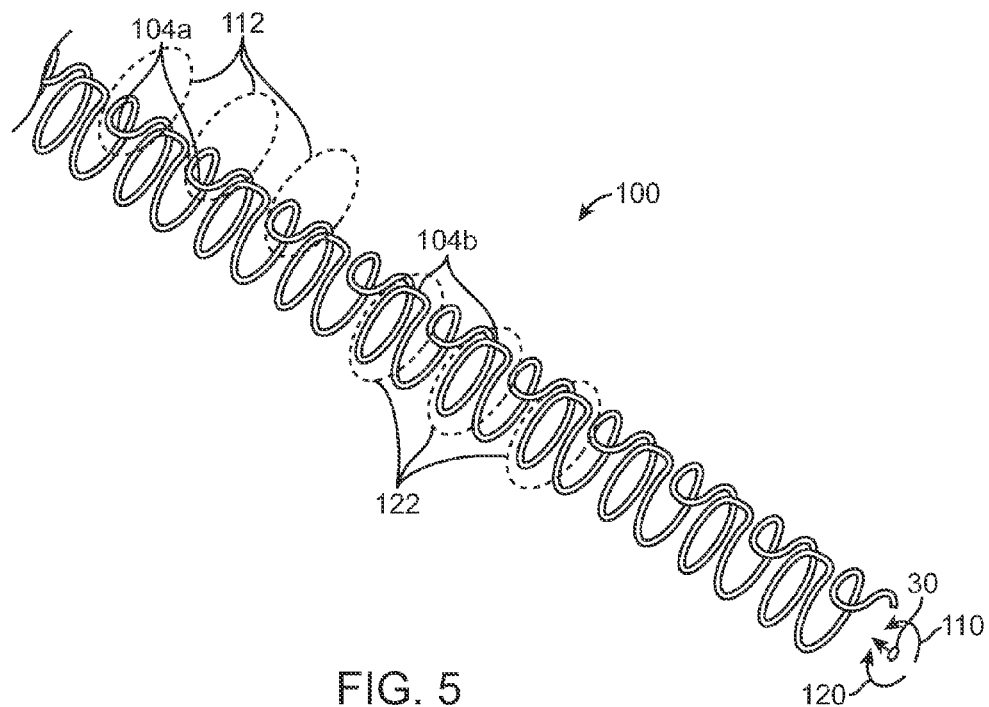
FIG. 5 is a perspective view of a wire structure of an elastic introducer according to an aspect of the disclosure.
Figure 6:
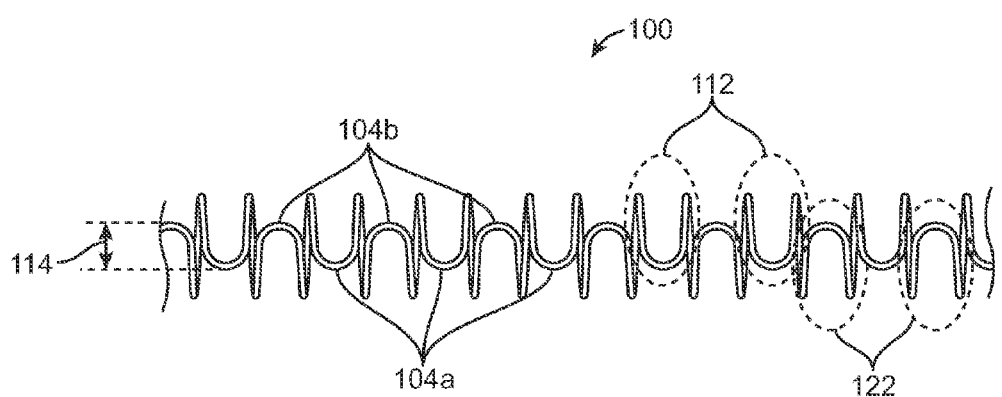
FIG. 6 is a top view of a wire structure of an elastic introducer according to an aspect of this disclosure.

Referring now to FIGS. 5-6, along the length of elastic introducer 10, the straight portions of wire structure 100 are curved about longitudinal axis 30 into a C-shaped wire structure 103 forming a series of non-continuous circumferential loops. To form the non-continuous circumferential loops, a first loop portion 112 of straight portions 102a and 102b joined by first bent end portion 104a is curved in a first radial direction 110. A second loop portion 122 of straight portions 102a and 102b joined by second bent end portion 104b is curved in a second radial direction 120. First loop portions 112 and second loop portions 122 form a series of alternating non-continuous circumferential loops extending along longitudinal axis 30. In one aspect of the invention, in a collapsed configuration of elastic introducer 10, first loop portions 112 and second loop portions 122 overlap longitudinally as demonstrated by wire overlap region 114. In one aspect of the invention, when elastic introducer 10 is in a collapsed configuration, first loop portions 112 are positioned within second loop portions 122 in wire overlap region 114 such that the second loop portions 122 cover the first loop portions 112. In an alternate aspect of the invention, when elastic introducer 10 is in a collapsed configuration, first loop portions 112 and second loop portions 122 do not overlap and do not include a wire overlap region 114.

Figure 7:
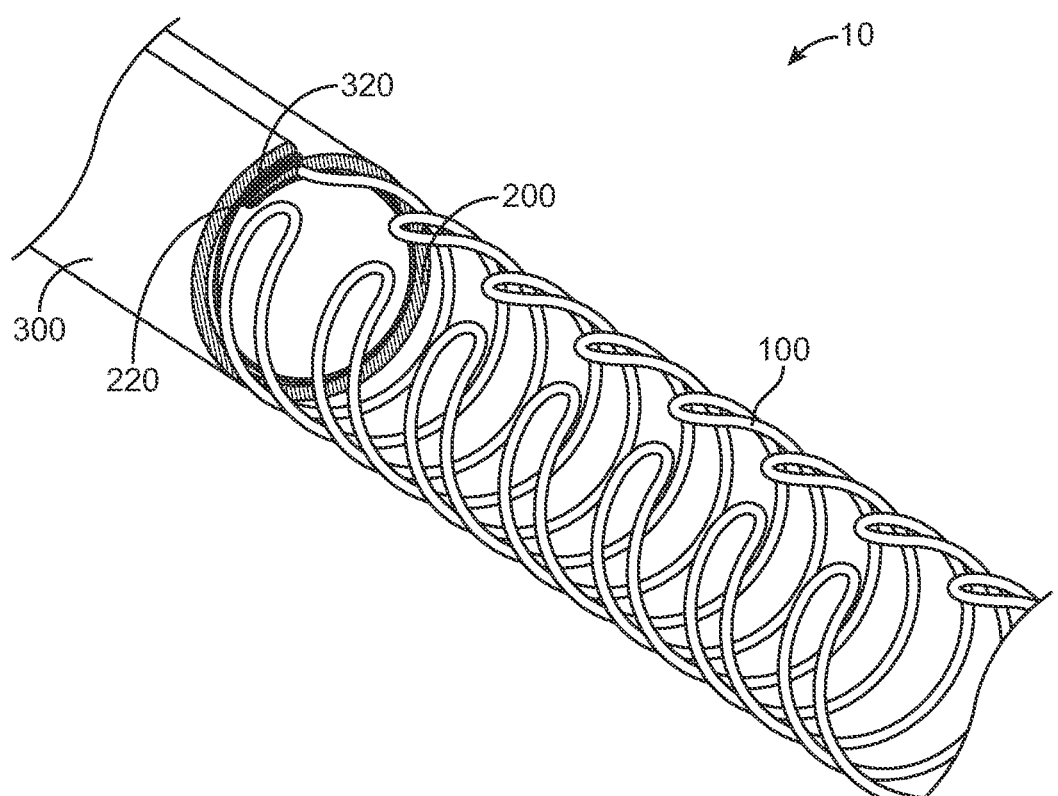
FIG. 7 is a perspective and cut away view of an elastic introducer according to an aspect of this disclosure.
Figure 8:
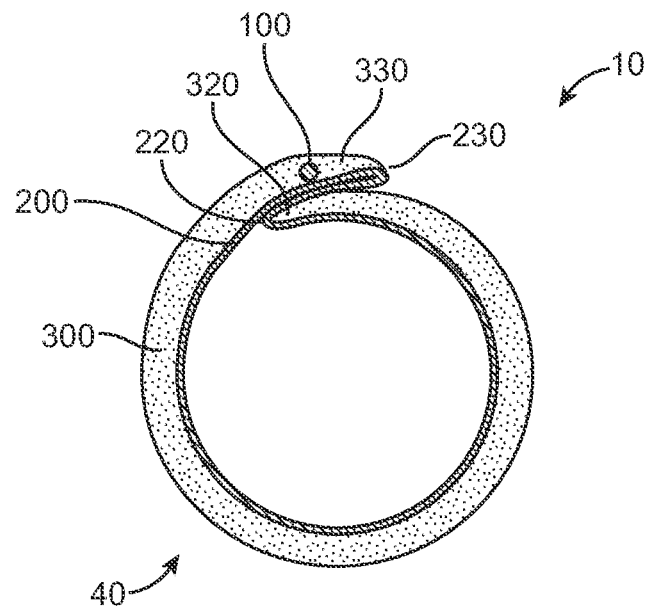
FIG. 8 is a sectional view of an elastic introducer according to an aspect of this disclosure.

Referring now to FIG. 7, elastic introducer 10 is shown in a collapsed configuration where wire structure 100 does not include a wire overlap region 114. In this aspect, second loop portions 122 extend slightly beyond inner fold 220 and inner edge 320.

Referring now to FIGS. 8-14, elastic introducer 10 is designed to allow for local expansion and subsequent recoil to reduce trauma to a patient's vessel. While introducing a transcatheter device, elastic introducer 10 can transition from a collapsed state 40 prior to accommodating transcatheter device 400, an expanded state 50 to accommodate transcatheter device 400, and a reduced state 60 after passage of transcatheter device 400. The diameter of elastic introducer 10 increases in expanded state 50 to accommodate transcatheter device 400. This increase in diameter is accomplished by first loop portions 112 and second loop portions 122 of wire structure 100 and inner edge 320 and outer edge 330 of jacket 300 diverging circumferentially to increase the effective diameter of elastic introducer 10. As elastic introducer 10 increases in diameter, inner fold 220 and outer fold 230 are flattened to allow liner gap portion 240 to span across jacket gap 340. Thus, liner gap portion 240 extends across jacket gap 340 and maintains a circumferentially continuous structure.

Arrow 410 shows the direction of travel of transcatheter device 400 through elastic introducer 10. Expanded state 50 of elastic introducer 10 is limited to the portion of elastic introducer 10 that surrounds transcatheter device 400. As transcatheter device 400 is moved distally in the direction of arrow 410, distal portions of elastic introducer 10 transition to expanded state 50 to accommodate transcatheter device 400. Furthermore, proximal portions of elastic introducer 10 transition to reduced state 60 following passage of transcatheter device 400.

After passage of transcatheter device 400, elastic introducer 10 recoils and reduces in diameter to reduced state 60, proximal to transcatheter device 400. The recoil and reduction in diameter is accomplished by the elasticity of wire structure 100. The elasticity of wire structure 100 allows first loop portions 112 and second loop portions 122 of wire structure 100 and inner edge 320 and outer edge 330 of jacket 300 to converge circumferentially and to reduce the effective diameter of elastic introducer 10. As elastic introducer 10 reduces in diameter, inner fold 220 and outer fold 230 are again utilized to allow outer edge 330 to partially cover the liner gap portion 240.

In one aspect of the invention, the diameter of elastic introducer 10 in the reduced state 60 is equal to the diameter of elastic introducer 10 in the collapsed state 40. In an alternate aspect of the invention, the diameter of elastic introducer 10 in the reduced state 60 is greater than the diameter of elastic introducer 10 in the collapsed state 40. In one aspect of the invention, elastic introducer 10 expands from a diameter of approximately 15 FR to approximately 19 FR. In an alternate aspect of the invention, elastic introducer 10 expands from a diameter of approximately 13 FR to approximately 18 FR.

In one aspect of the invention, elastic introducer 10 can be sized for a transcatheter heart valve procedure and can be used with a transcatheter heart valves and delivery system such as those described in U.S. application Ser. No. 12/870,567; and U.S. Patent Publication Nos. 2006/0265056, 2007/0239266, 2007/0239269, and 2011/0251681, which are incorporated herein by reference in their entirety. For example, transcatheter device 400 can be an aortic valve prosthesis.

Figure 15:
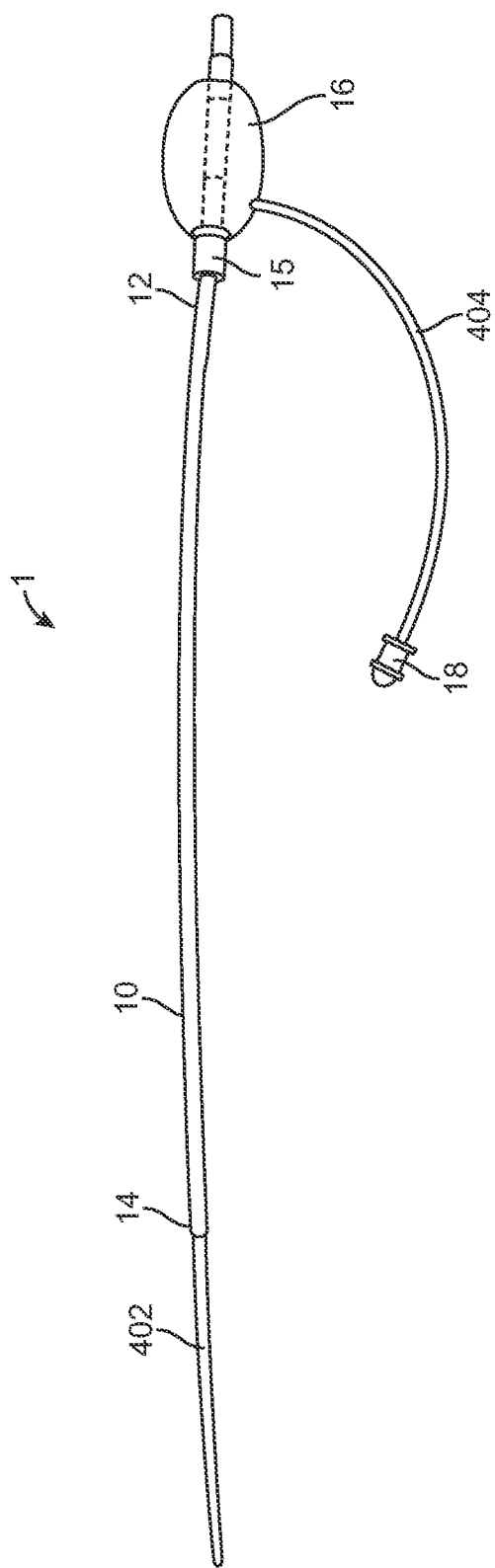
FIG. 15 is a top view of an introducer system according to an aspect of this disclosure.

In alternate aspects of the invention, elastic introducer 10 can be sized for endoscopic procedures, procedures in the coronary vessels, or procedures in the peripheral vessels, Introducer system 1 is shown in FIG. 15. Introducer system 1 includes elastic introducer 10, a proximal end 12, a dilator 402, a flush tube 404, a proximal hub including a valve 16, and a Luer connector or stopcock 18. In one aspect of the invention, dilator 402 is 14.5 FR. In another aspect of the invention, proximal end 12 is non-expandable.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A surgical access device comprising:
   a sheath having an expandable section comprised of
      a circumferentially continuous inner layer of a biocompatible material;
      a non-circumferentially continuous wire structure defining along a length of the expandable section a plurality of first loop portions extending in a first radial direction and a plurality of second loop portions extending in a second radial direction, wherein respective first loop portions longitudinally overlap with respective second loop portions when the expandable section is in a collapsed configuration and wherein a longitudinal gap extends between respective first loop portions and respective second loop portions when the expandable section is in an expanded configuration; and
      a non-circumferentially continuous outer layer of a biocompatible material, the outer layer being connected to the wire structure and to the inner layer to form a wall of the expandable section, the outer layer having a longitudinal gap when the expandable section is in the expanded configuration and having an overlap region when the expandable section is in the collapsed configuration.

2. The surgical access device of claim 1, wherein the wire structure is curved to form a C-shape in a radial direction.

3. The surgical access device of claim 1, wherein the wire structure has a sinusoid shaped wire pattern along a longitudinal direction.

4. The surgical access device of claim 1, wherein the wire structure has a square shaped wire pattern along a longitudinal direction.

5. The surgical access device of claim 1, wherein the sheath further comprises a proximal section having a first outer diameter that is greater than a second outer diameter of the expandable section.

6. The surgical access device of claim 5, wherein the sheath further comprises a transition section longitudinally positioned between the proximal section and the expandable section, the transition section providing a tapered outer diameter from the first outer diameter of the proximal section to the second outer diameter of the expandable section.

7. The surgical access device of claim 1, wherein when the expandable section is in the collapsed configuration a first fold in the inner layer is disposed around a first edge of the outer layer.

8. The surgical access device of claim 7, wherein when the expandable section is in the collapsed configuration a second fold in the inner layer is disposed inward of a second edge of the outer layer.

9. A locally expandable surgical access device comprising:
   a sheath having an expandable section comprised of
      a curved non-circumferentially continuous wire structure extending along a length of the expandable section, wherein a longitudinal gap is defined between first end portions of the wire structure and opposing second end portions of the wire structure in a collapsed configuration of the expandable section, and wherein a width of the longitudinal gap increases in an expanded configuration of the expandable section;
      a non-circumferentially continuous outer layer connected to the wire structure, the outer layer having a longitudinally-extending first edge and a longitudinally extending second edge, wherein a longitudinal gap is defined between the longitudinally extending first and second edges of the outer layer in the expanded configuration of the expandable section and wherein an overlap region of the outer layer is defined between the longitudinally extending first and second edges of the outer layer in the collapsed configuration of the expandable section; and
      a circumferentially continuous inner layer connected to the outer layer to form a wall of the expandable section, wherein the inner layer and the outer layer are formed from biocompatible materials.

10. The locally expandable surgical access device of claim 9, wherein the expandable section is expandable from a first diameter to a second diameter to allow passage of a transcatheter medical device.

11. The locally expandable surgical access device of claim 10, wherein the expandable section is reducible from the second diameter to a third diameter.

12. The locally expandable surgical access device of claim 11, wherein the third diameter is equal to the first diameter.

13. The locally expandable surgical access device of claim 9, the expandable section further comprising a first fold in the inner layer disposed around the first edge of the outer layer in the collapsed configuration of the expandable section.

14. The locally expandable surgical access device of claim 13, the expandable section further comprising a second fold in the inner layer disposed inward of the second edge of the outer layer in the collapsed configuration of the expandable section.

15. The locally expandable surgical access device of claim 14, wherein the first fold and the second fold of the inner layer unfold and flatten in the expanded configuration of the expandable section.

16. The locally expandable surgical access device of claim 9, wherein the wire structure includes a plurality of straight portions and a plurality of curved portions and wherein the first and second end portions are defined by the plurality of curved portions.

17. The locally expandable surgical access device of claim 9, wherein the wire structure has a sinusoid pattern.

18. The locally expandable surgical access device of claim 9, wherein the sheath further comprises a proximal section having a first outer diameter that is greater than a second outer diameter of the expandable section.

19. The locally expandable surgical access device of claim 18, wherein the sheath further comprises a transition section longitudinally positioned between the proximal section and the expandable section, the transition section providing a tapered outer diameter from the first outer diameter of the proximal section to the second outer diameter of the expandable section.

* * * * *